United States Patent [19]
Johnson

[11] Patent Number: 5,807,099
[45] Date of Patent: Sep. 15, 1998

[54] APPARATUS FOR LAMINATING AND AESTHETICALLY APPEARING PORCELAIN VENEER TO THE EXTERIOR FRONT SURFACE OF A PERSON'S FRONT TOOTH

[76] Inventor: Paul W. Johnson, 5103 46th N.E., Seattle, Wash. 98105

[21] Appl. No.: 576,257

[22] Filed: Dec. 21, 1995

Related U.S. Application Data

[62] Division of Ser. No. 310,636, Sep. 22, 1994, Pat. No. 5,501,600.

[51] Int. Cl.⁶ ............................................. A61C 5/10
[52] U.S. Cl. .............................. 433/25; 433/227; 72/60
[58] Field of Search ........................ 433/25, 218, 219, 433/223, 227; 72/57, 60

[56] References Cited

U.S. PATENT DOCUMENTS

| | | | |
|---|---|---|---|
| 4,734,173 | 3/1988 | Walter et al. | 433/223 |
| 4,742,704 | 5/1988 | Wellington et al. | 72/57 |
| 4,829,807 | 5/1989 | Nacke | 72/57 |
| 5,014,532 | 5/1991 | Shoher et al. | 433/223 |
| 5,028,235 | 7/1991 | Smith | 433/223 |
| 5,073,113 | 12/1991 | Hornig | 433/223 |
| 5,232,365 | 8/1993 | Ikehara | 433/223 |
| 5,445,770 | 8/1995 | Adam et al. | 433/223 |
| 5,501,600 | 3/1996 | Johnson | 433/227 |
| 5,624,263 | 4/1997 | Babaian | 433/223 |

Primary Examiner—Edgar S. Burr
Assistant Examiner—Steven S. Kelley
Attorney, Agent, or Firm—Roy E. Mattern, Jr.

[57] ABSTRACT

When a dental patient is having one or more of his or her front teeth aesthetically improved, when a dentist cements thereon a porcelain veneer, which becomes a porcelain laminate extending across the front surface of the patient's tooth, the method steps followed and the equipment used have been improved. The improvements center both on obtaining more quickly and more accurately a noble metal foil matrix, which conforms to the front surface of the front tooth die of the patient, and on applying the porcelain ceramic slurry on the conformed noble metal material, to compensate for the shrinking of the porcelain during the firing thereof. The improved equipment is a forming machine which utilizes a constant pressure source of compressed air to move a piston in a cylinder, with the piston moving one metal die to contact another metal die, each die having an aligned rubber insert, and each rubber insert having an alike aligned receiving space. A patient's front tooth die with a pin, having its front face covered by a pre-sized noble metal foil, is placed within a thin plastic cover.

17 Claims, 8 Drawing Sheets

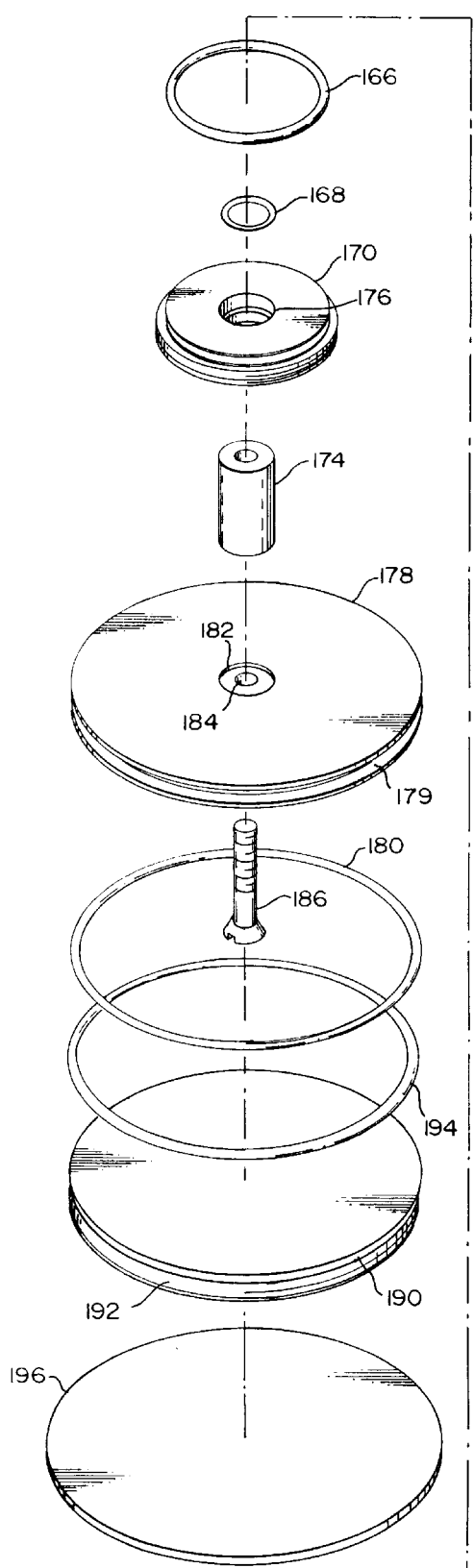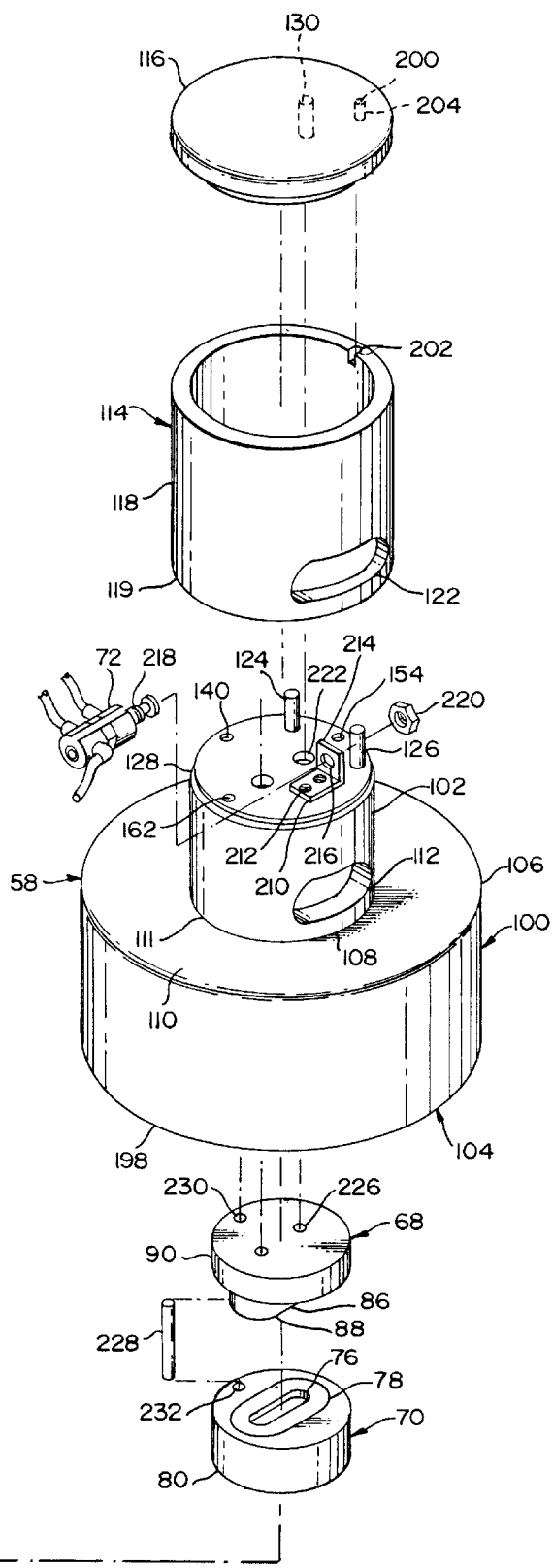
FIG. 4

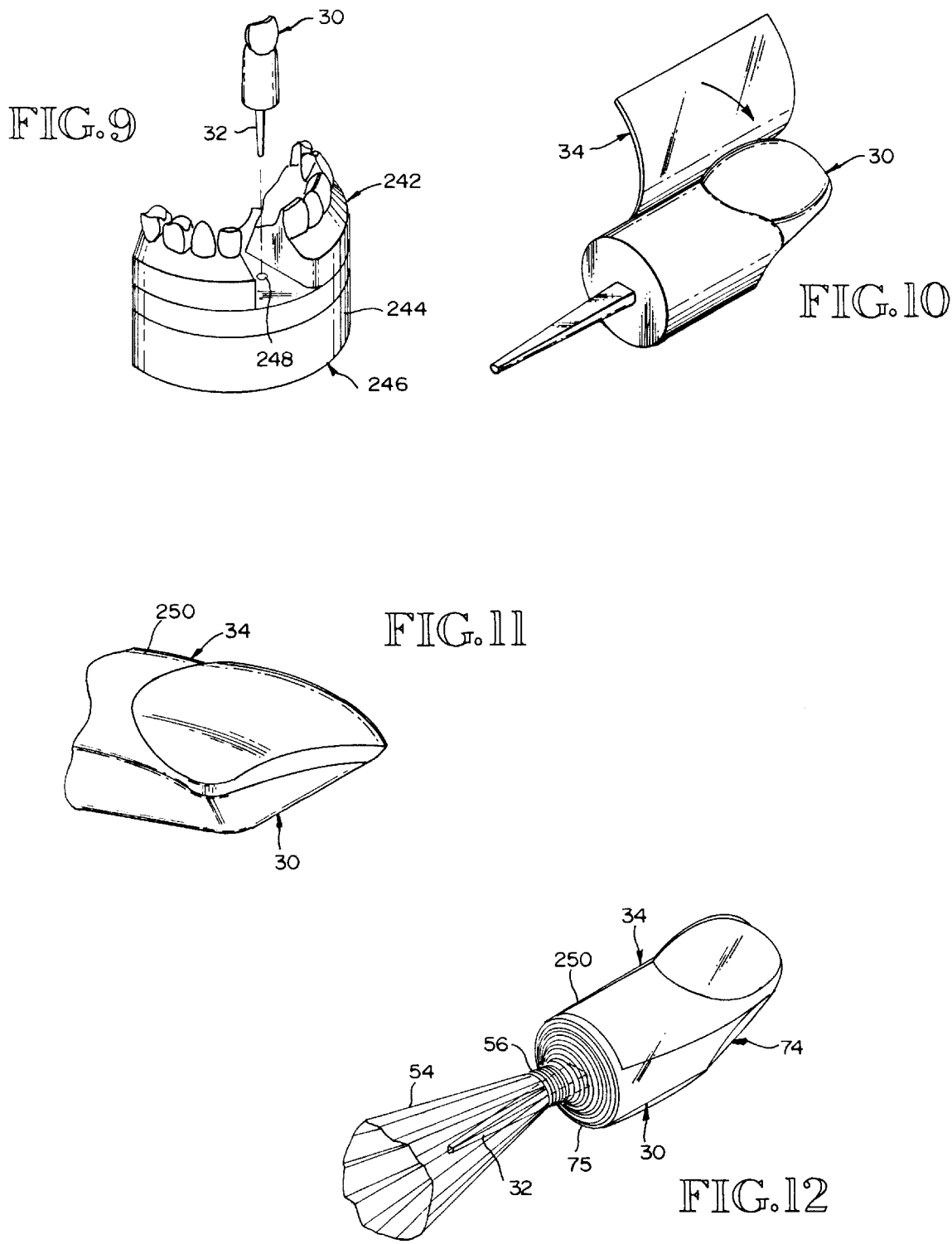

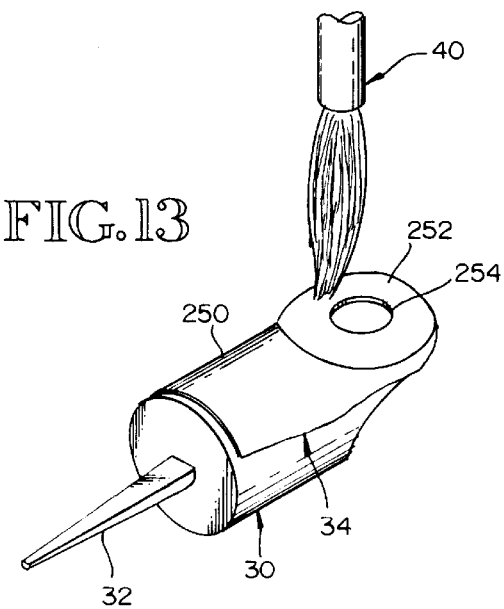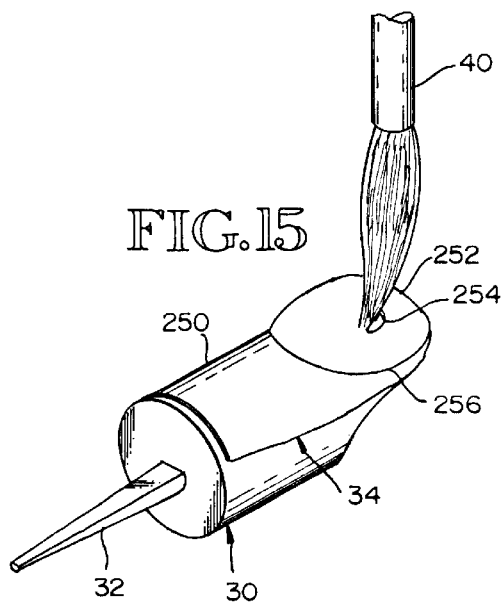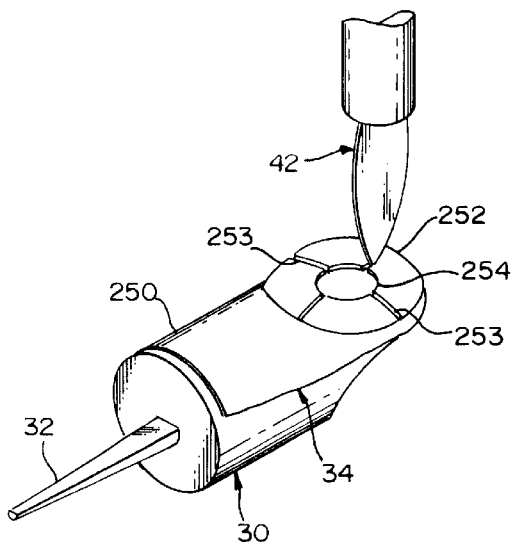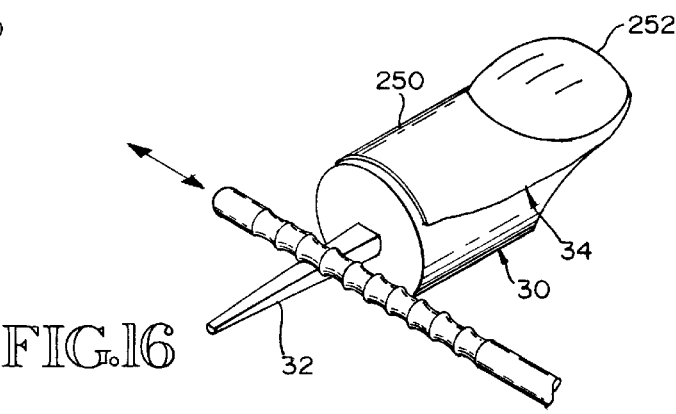

APPARATUS FOR LAMINATING AND AESTHETICALLY APPEARING PORCELAIN VENEER TO THE EXTERIOR FRONT SURFACE OF A PERSON'S FRONT TOOTH

CROSS REFERENCE

This is a Division application based on Ser. No. 08/310,636, filed Sep. 22, 1994 now U.S. Pat. No. 5,501,600 of same title and same Applicant.

BACKGROUND

Improving the appearance of one or more of a person's anterior teeth has been undertaken previously by adding an aesthetically appearing porcelain veneer to a respective tooth or teeth. By way of example, Thomas S. Greggs, in his U.S. Pat. No. 4,473,353, illustrates and describes his method for cosmetic restoration of anterior teeth. He custom made a glazed porcelain labial veneer for a patient's tooth. Thereafter, he chemically and mechanically bonded the glazed porcelain labial veneer to the respective patient's tooth, to provide a healthful and long lasting cosmetic restoration of desired color, shape, and aesthetic appearance.

More particularly, Thomas S. Greggs, and his assistants, including a lab technician, created and applied the aesthetically appearing porcelain veneer to a respective tooth utilizing a method which he described as follows:

Conventional crown and bridge impression materials were used in taking an impression of the patient's teeth, and recordings were made pertaining to the patient's bite, shade and other pertinent data;

The patient's impression was filled by pouring in die stone materials;

A Pindex model was made, pinning all teeth to be veneered, as well as adjacent teeth;

Each tooth die was undercut at the cervical extension, trimmed at the marginal areas of the regions to be veneered and hardened, so as to replicate the identical structure of the cosmetically defective tooth;

A triangular shaped platinum foil was placed over the labial surface of the tooth die with the apex pointed downward and forming a tab portion which extends below the gingival margin. The base of the triangular shaped foil was folded over the incisal edge of the die and at least partially around the proximal surfaces, in such a manner as to form a snugly fitting, but hingedly removable at the top, foil sheath on the tooth die. For added retention, the foil was adhered to the previously made undercut;

The platinum matrix was removed from the die using the tab portion formed by the foil apex and pulling the foil sheath hingedly off the incisal edge of the die;

The platinum matrix was then held over a Bunsen burner flame to decontaminate it;

The platinum matrix was then reapplied to the die;

Thereafter the platinum matrix was burnished thereon in some way which was not explained;

Porcelain was then applied to the labial surface of the platinum matrix using a brush, starting at the cervical undercut and working up to the incisal edge, and in so doing, the building up of the porcelain was undertaken thinly and uniformly;

The platinum matrix, also called the foil matrix with the porcelain was removed from the tooth die and placed on a tray, then in turn placed in a furnace for firing;

The foil matrix and baked porcelain veneer thereon were then replaced on the tooth die. The marginal areas of the porcelain veneer were finished. Then the porcelain veneer was contoured into an aesthetic shape, and the labial antomy was carved;

The foil matrix and the porcelain veneer were removed from the tooth die for the last time;

The porcelain veneer was cleaned ultrasonically;

Then the porcelain veneer was stained and glazed using conventional techniques to conform to the shade characteristics selected in respect to the patient's teeth;

The room temperature foil matrix and porcelain veneer were placed in distilled water for one minute. Then using tweezers, the foil was gently removed from the porcelain veneer;

The intaglio, or inside surface, of the porcelain veneer was then etched, usually by air abrasion, to promote bonding thereof to the enamel tooth surface;

Then the appropriate enamel surfaces of the patient's tooth were etched with an acid gel formulation, to create micropores and thereby promote bonding;

The intaglio surface of the porcelain veneer was then coated with a thin layer of light curing bonding agent;

A similar layer of the bonding agent was applied to the etched enamel bonding surface of the patient's tooth;

Both of these layers of bonding agent were polymerized by light curing;

A coating of dental filler material was then applied to either the patient's tooth or the intaglio surface of the porcelain veneer;

Then the porcelain veneer was placed onto the patient's tooth;

Excess filler material was trimmed away, and the filler material was polymerized by a second application of light; and Then the dentist finished the proximal and incisal margins to provide a smooth restoration surface.

Mr. Thomas S. Greggs in his U.S. Pat. No. 4,473,353 said the foil matrix was burnished over the tooth die, without describing how the burnishing might be done. In this respect of the forming of the foil matrix, in connection with a new technique for constructing a ceramic to metal crown from a metal foil coping, as disclosed in U.S. Pat. Nos. 4,459,112 and 4,492,579, Messrs. Itzhak Shoker and Aharon E. Whiteman illustrated and described their dental swager, in their U.S. Pat. No. 5,014,532. To adapt a dental foil coping to a die of a tooth to be restored, their dental swager was used. It had a male punch, and a female base support in which the die of the tooth to be restored was mounted with the metal foil coping placed over the tooth die. An insert was located in the male punch for transferring the force applied to the punch to the metal foil coping and the tooth die. The insert was composed of a solid material having an elastic memory. Also a shock absorber, having a putty-like consistency, separated this insert from the male punch.

In further reference to how a foil matrix might be burnished, Messrs. Danny R. Clark and Asami Tanaka, in their U.S. Pat. No. 4,794,774, illustrate and describe their method of preparing a dental restoration. A die, of a prepared patient's tooth requiring a dental restoration, is fitted with a metal foil. Initially, the metal foil is fitted to the tooth die by using standard folding and crimping techniques. However, the close tolerances required are not as yet met. Therefore the metal foil covered tooth die is then placed in a flexible, fluid impermeable sack and the sack is sealed. Then the sealed sack with the metal foil covered tooth die, is placed in the main chamber of an isostatic press. This main chamber is filled with water and a cap is partially threaded into place. A pump is operated to increase the pressure and drive out air through the partially threaded cap gap. When water appears, the cap is tightened and the pressure builds up. Thereafter, the fluid, preferably water, transmits the pressure isostatically against the sealed sack 14 to uniformly press the metal foil against the tooth die. The isostatic pressure is in the range of 1000 to 2500 p.s.i. When the forming is completed, the pressure is released from the system, and the sack 14 is removed from the chamber, and the metal foil covered tooth die is removed from the sack. A superior uniform fit of the metal foil to the tooth die is obtained.

In earlier days in forming gold crowns for teeth, dental swaging apparatus of various types were utilized, as illustrated and described in U.S. Pat. Nos.: 582,872 of 1897; U.S. Pat. No. 889,085 of 1908; U.S. Pat. No. 946,962 of 1910; U.S. Pat. No. 1,794,197 of 1931; and U.S. Pat. No. 1,883,968 of 1932.

In utilizing hand burnishing methods, oftentimes it becomes very difficult and time consuming to create a good fit between the noble metal foil and the front face of a patient's tooth die. When hand burnishing is being done on one side, then the opposite side of the noble metal foil is affected, often losing its previous good conformance to the tooth die. A compromise fit is then sometimes considered acceptable, yet the final fitting to the patient's tooth may not last for as long a period of time as originally intended.

When attempts are made to form the noble metal foil by using hammer like blows against dies, bearing in turn on the noble metal foil covering a patient's tooth die, quite often the force used is excessive, and the patient's tooth die is destroyed. Such destruction results in the need to create another patient's tooth die causing the unwanted delay and unwanted related cost.

To avoid such difficulties of conforming the noble metal foil by hand burnishing or by excessive hammer like forces, some dental persons use the investment casting method. The patient's tooth die, used in the investment casting method, directly receives the porcelain slurry and therefore it is fired with the porcelain. Considerable time is consumed in preparing the patient's tooth die which must withstand the high firing temperatures. Moreover, when the decision is made that the porcelain veneer is ready for fitting, then this high temperature resistant patient's tooth die is broken away from the porcelain veneer. If the resulting fitting to the patient's front tooth is not considered satisfactory, then a new patient's tooth die must be made, causing an unwanted delay and an unwanted related cost, when this investment casting method has been used.

These inventors and many others have led the way to constantly improve the practice of dentistry. In particular, in reference to the illustrations and descriptions set forth in these patents, their inventions serve to be useful in understanding how today patients' teeth needing cosmetic restoration to gain or to regain their aesthetic appearance, are restored. As always realized, there are still better ways being sought to improve such tooth cosmetic restorations.

SUMMARY

In respect to better ways to improve tooth cosmetic restorations to gain or to regain their aesthetic appearances, improvements, as illustrated and described herein, have been made. In particular the major improvement has been undertaken in respect to the burnishing step or operation, wherein a machine utilizing air pressure is operated in performing this burnishing step, also referred to as a swaging step or the conforming step. By closely following the entire method and utilizing this machine, which is thoroughly illustrated and described herein, the overall time, skill level, and labor involved is substantially reduced, while maintaining quality, in cosmetically restoring a patient's tooth or teeth.

The method is again briefly described and the machine is referred to more extensively as follows:

A patient meets a dentist to ascertain what might be done to make one or more of her or his front teeth more aesthetically acceptable;

A decision is made that a porcelain veneer is possible, with or without other dental preparations being undertaken, to prepare the tooth to receive a porcelain veneer, or laminate. A full crown, otherwise requiring a total cutdown of a tooth is not required;

An impression is taken of the patient's teeth using any suitable crown and bridge impression material. Polyvinyl silloxane is considered the best material, because two pours are to be undertaken to make duplicate models.

By pouring gypsum die stone materials into the impression of the patient's teeth, two models of hard gypsum die stone are fabricated. The first model remains as a record of how the patient's teeth appeared at the outset of this dental work, and this first model is kept as the master model.

The second model is the working model and it is trimmed for final spacing and fit. Then, an individual model tooth, or several individual model teeth are removed by cutting away, to become tooth dies, each of which is fitted with a respective dowel pin and replaced, until a subsequent time of use.

Platinum or palladium foil, annealed to be dead soft, serve as the noble metal foil, and subsequently only platinum will be referred to, is cut to cover the front surface of the front tooth die. This platinum foil is so cut to cover the height of tooth contours, yet leaving five to six millimeters, i.e. 5–6 mm, of excess or free platinum foil beyond the labial gingival location on the front tooth die. This extra, so-called free platinum foil material is used, as a gripping place or apron which is used later, when carrying the platinum foil, then having, over the tooth locale, a porcelain layer on it, and then also having been removed from the tooth die, to a resting place on a firing tray;

The cut to size platinum foil is quickly positioned on the tooth die and held in place using a thin saran like plastic cover to hold this noble metal foil properly in place and to avoid any subsequent possible contamination of this noble metal foil;

This saran like plastic cover is in turn held in place by wrapping its excess end with dental floss, acting as a string, where it extends over a portion of the dowel pin;

Additional portions of dental floss, i.e. string, are used at this same location to fill in a tapered like volume formed by the sharp angle, that has been created between the shoulder of the front tooth die and the extending dowel pin supporting the front tooth die. This additional tapered dental floss wrapping serves to prevent the otherwise possible breaking of portions of the front tooth die.

Then at this time the forming machine, utilizing the specified constant air pressure, is utilized in accomplishing in ten seconds, what has been previously undertaken by using a hand tool during a long intensive burnishing step. This forming machine is supplied with compressed air in the range of 85 to 110 p.s.i., and preferably the specified pressure is 100 p.s.i. The piston area is large in comparison to the reduced area, where a top male die having a rubber insert, or a rubber-like silicone method, in turn having a receiving space, is located and not movable, and the lower female die also having a rubber or rubber-like insert, in turn having a receiving space, is moved as the piston moves, when these dies become effective in accurately conforming the platinum foil to the front surface of the tooth die. By using the lower pressure of 100 p.s.i. acting on the relatively large diameter piston area, a substantial force is created. Then this force, distributed throughout the smaller area of the active dies, i.e. like a smaller piston area, increases the effective conforming pressure. Yet this increased conforming pressure is kept well below any pressure, which would result in the destruction of the patient's tooth die.

By the rotation of the top portion of this forming machine, an entry is opened, while the air pressure remains ineffective. Through this entry, the covered and wrapped platinum foil and front tooth die are placed in a receiving space of a rubber insert of the movable lower female die, which is secured to the piston. This arrangement or bundle of the covered and wrapped platinum foil and front tooth die is at this time located directly below a like sized receiving space of a rubber insert in the stationery top male die. Then upon a reverse rotation of the top portion of this forming machine, the entry is closed. Thereafter the air pressure becomes effective, as pressurized air is admitted to move the piston, and consequently move the lower female die into effective contact with the stationary top male die. There is no chance of a person's fingers being in a dangerous position. This closing movement causes the rubber of the respective inserts to effectively apply a compressive force completely around the arrangement or bundle of the wrapped and wound platinum foil. This is referred to as an orbital or isostatic compressive force. In this way the metal foil is quickly and accurately conformed, i.e. fitted, to the front tooth die. After ten seconds of forming, the opposite rotation of the top portion of this forming machine is undertaken, which automatically stops the flow of compressed air, vents the compression air, and thereafter presents the open entry once again for the removal of the arrangement or bundle of the covered and wrapped platinum foil from the receiving space, also called a molded groove or cavity, of a vulcanized rubber insert, a gum rubber insert, or a silicone rubber-like material insert of the lower female die.

The dental floss is unwound or unwrapped to free the thin plastic cover and it is removed;

The platinum foil is inspected to make sure the platinum is completely adapted to the front surface of the front tooth die. If this platinum foil is properly adapted to the front tooth die, then the surface texture of the front tooth die will be evident through observing the surface of the platinum foil;

If desired, before its use or at a later time to insure its dead soft quality, also the platinum foil can be handled with tweezers and placed in a furnace and annealed by reaching a bright red heat temperature. After annealing, the platinum foil, by using tweezers is placed on the gypsum tooth die;

Then with the platinum foil in place on the tooth die, any possible folds, or ripples, which may be left in the platinum foil, can be hand burnished flat and smooth. Generally, the hand burnishing will warp the platinum foil matrix;

Therefore, the platinum foil and front tooth die are covered and wrapped again using the saran like plastic and dental floss;

Then this arrangement or bundle is returned to the forming machine and accurately formed, i.e. swaged or conformed, during the ten second cycle, and then removed;

Unwrapping and uncovering follows to gain access to the platinum foil also referred to as the platinum foil matrix, which is now totally free from fold lines, and it is removed from the front tooth die. Then the noble metal foil is now ready for the application of a porcelain slurry;

By brushing, a porcelain slurry is applied as a coating over the platinum foil matrix, while leaving a central area clear, i.e. uncovered and referred to as a bald area or bald spot, to later be filled in when compensating for the shrinkage of the porcelain upon firing;

Partial drying of the porcelain slurry is undertaken by using tissue to absorb excess water from the porcelain slurry;

Cutting the partially dried first application of this porcelain slurry using a porcelain knife at spaced locations is also undertaken, so the cut areas or volumes will later be utilized when compensating for the shrinkage of the porcelain during firing;

Firing is undertaken in a furnace of the porcelain slurry coating on the platinum foil matrix, i.e. the noble metal foil matrix;

By brushing again, more porcelain slurry is added to cover the bald central area, to fill in the cut areas, and to cover other areas, and in doing so to complete respective contours, and at this time a lighter shade of porcelain slurry is applied at and along the incisal edge, i.e. biting surface, of the porcelain veneer being created;

Firing is undertaken in a furnace again of the porcelain slurry, the porcelain, and the noble metal foil matrix;

Shaping of the labial, i.e. front, contour of the porcelain follows by using dental tools;

Further characterization, as necessary, is done of the front surfaces of the porcelain to resemble wanted features of the patient's original front tooth surface;

Firing is undertaken in the furnace again of the porcelain coating for a sufficient time to create the wanted glaze of the porcelain;

Removal follows of the platinum foil matrix from the porcelain veneer, also referred to as the porcelain laminate; preferably such removal is done in the presence of water;

overing the glazed labial surface of the porcelain veneer with a sticky wax is done to protect the glaze of the porcelain;

Roughening the interior surface of the porcelain veneer is done by sandblasting or etching;

Washing the porcelain veneer then removes the sticky wax;

Checking the fitting of the porcelain veneer to the patient's front tooth is done, and if the fit is excellent as expected; then Cementing the well fitting porcelain veneer to the patient's front tooth is undertaken creating the porcelain laminate in place.

By using this method centering on the operation of the forming machine, which utilizes the metal dies with the rubber or rubber-like inserts, and is powered by compressed air at a like specified pressure each time, the processing time, the skill level, and labor has been substantially reduced in the making and fitting of porcelain veneers on patients' teeth to make the respective restored teeth aesthetically pleasing in their appearance for many years.

DRAWINGS

The improved method and apparatus for adding an aesthetically appearing porcelain veneer to the exterior front surface of a person's front, i.e. anterior, tooth are illustrated in the drawings, wherein:

FIG. 1 is a perspective view of a table top, or bench top area, where the apparatus' tools and supplies are arranged for their utilization by a dentist and/or persons assisting a dentist in his or her restoration of the front surface of a patient's front tooth;

FIG. 2 is a perspective view of the forming machine shown on the left side of FIG. 1, which receives compressed air at a specified constant pressure to relatively move metal dies together, which each have rubber inserts with respective receiving spaces to position a noble metal foil portion, previously located over a tooth die, to create a noble metal foil matrix which matches the front surface of the front tooth die, and an entry is shown which remains open, when the air pressure source is shut off, to receive the noble metal foil portion and the front tooth die, and which closes before the air pressure source is turned on again, so as to prevent any possible injury to an operator's fingers;

FIG. 4 is a perspective exploded view illustrating the various parts of the forming machine illustrated in FIGS. 1 through 3;

Figure 5:
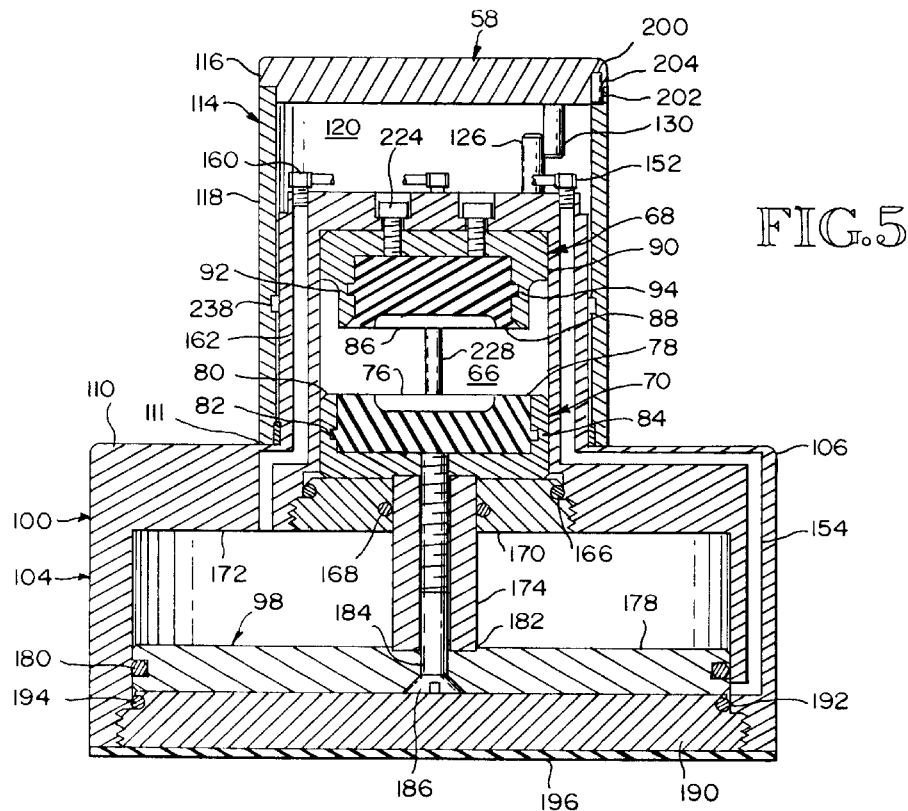
FIG. 5 is a cross-sectional view of the forming machine shown in FIGS. 1 through 4.
Figure 6:
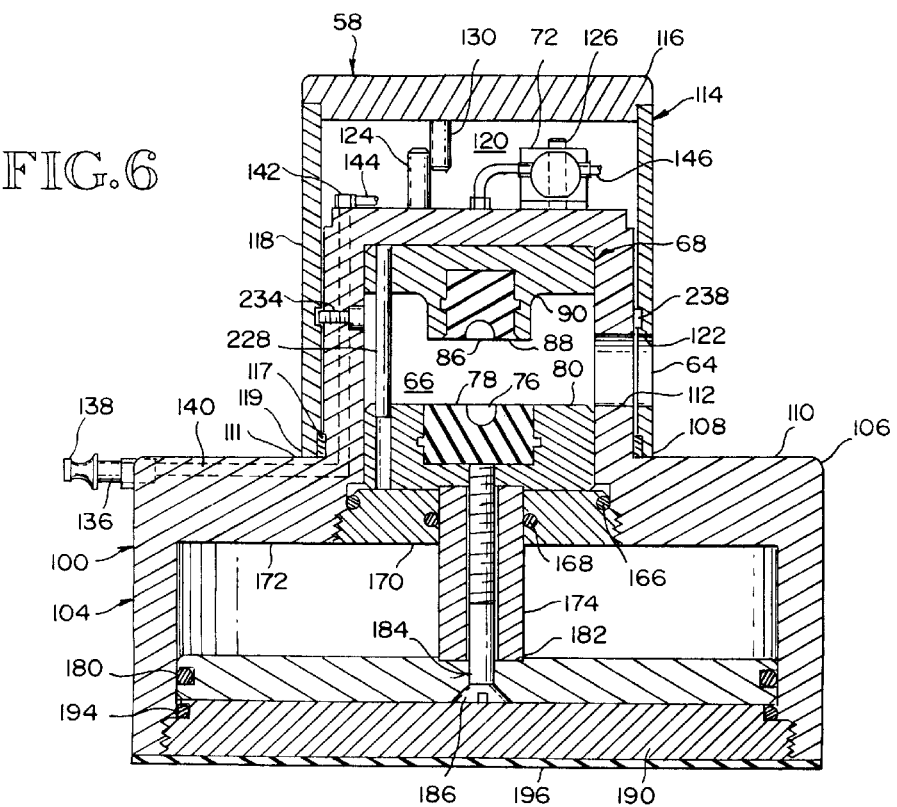
FIG. 6 is a cross-sectional view of the forming machine, similar to FIG. 5, but taken along a section line, which is at a ninety degree rotation from the section line, used as a reference for FIG. 5.
Figure 7:
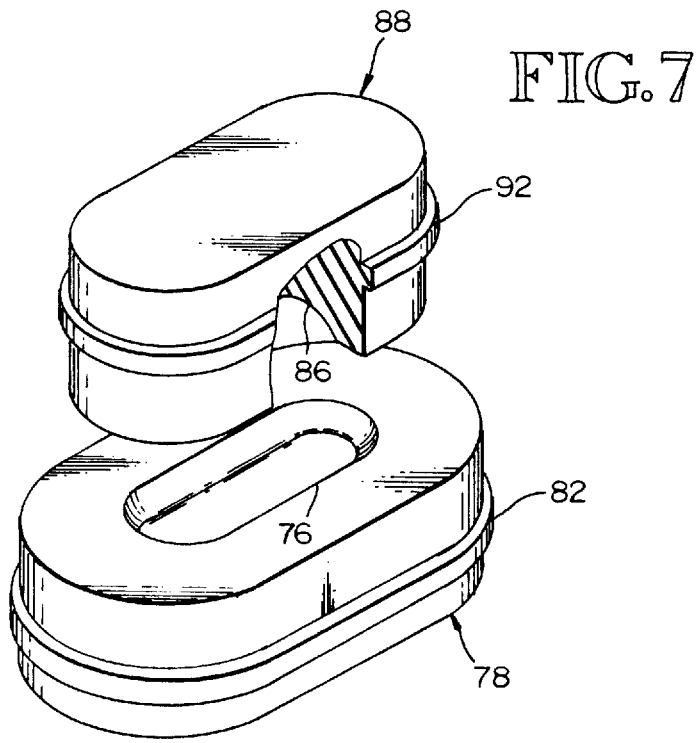
FIG. 7 is a perspective view of the two rubber inserts for the respective top male metal die and the lower female metal die, shown in their open positions in both FIGS. 5 and 6.
Figure 8:
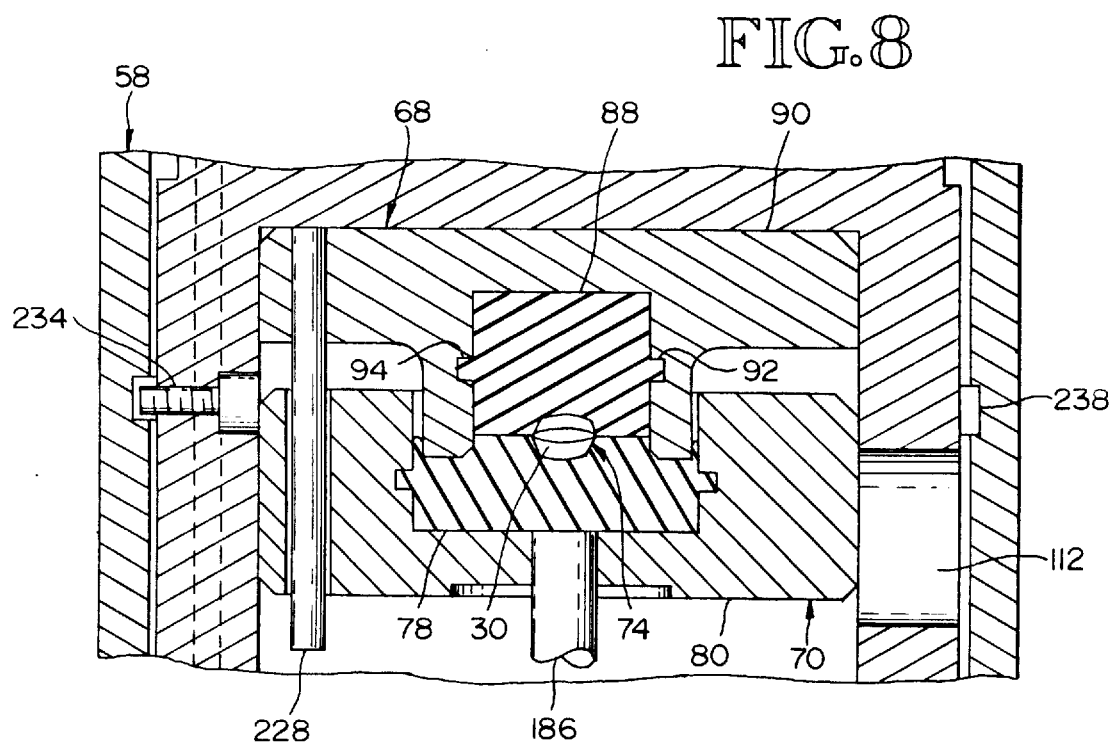

FIG. 8 is a partial cross-sectional view of the forming machine, shown in FIGS. 1 through 7, to show the positioning of the closed metal dies, as their rubber, or rubber-like inserts, shown in FIG. 7, have been moved together, serving to surround the noble metal foil and the front tooth die to conform the platinum metal foil or palladium foil to accurately fit the front surface of the front tooth die, which represents the front surface of the patient's front tooth, which is to be restored;

FIG. 9 is a perspective view of a gypsum die stone made by using an impression made of a patient's teeth, and indicating how one gypsum die tooth has been removed and fitted with a dowel pin, in reference to this working model; and this die tooth has a front surface, which matches the front surface of a patient's front tooth which needs restoring to improve the aesthetic appearance thereof;

FIG. 10 is a perspective view showing the start of the placement of a noble metal foil over the die tooth;

FIG. 11 is a perspective view showing how the noble metal foil has been placed over the die tooth and trimmed;

FIG. 12 is a perspective view illustrating how the die tooth, when covered with the noble metal foil, is then covered with clear Saran plastic, which is thereafter held in place by windings or wrappings of dental floss, wound in sufficient number, to serve as a tapered filler between the abrupt ninety degree edge of the gypsum tooth die and the dowel pin, and as not shown, later the excess saran plastic is trimmed away;

FIG. 13 is a perspective view of noble metal foil on the front tooth die, after the compression forming has occurred in the forming machine, as illustrated in FIG. 8, showing how the porcelain slurry is being applied by using a porcelain sable brush, and leaving uncovered a central area, referred to as a bald area, during this first application of the porcelain slurry, which later serves in compensating for the shrinkage of the fired porcelain;

FIG. 14 is a perspective view of the noble metal foil on the front tooth die which has been covered by the porcelain slurry, except for the bald area, as shown in FIG. 13, and then partially dried by absorbing excess water, generally by using a tissue, to the extent that the drier porcelain slurry then can be cut, using a porcelain knife, at selected spaced locations, which also later serve in compensating for the shrinkage of the fired porcelain.

Figure 17:
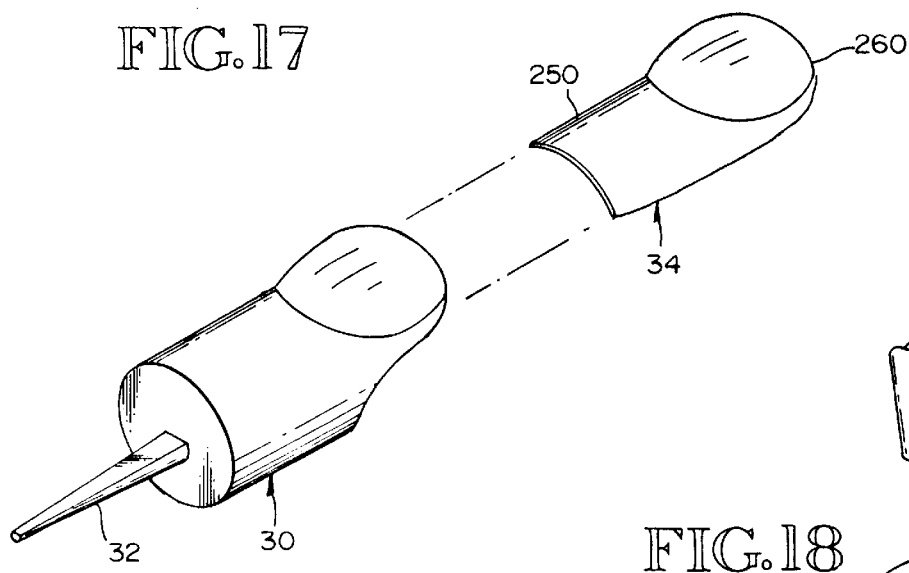
Figure 18:
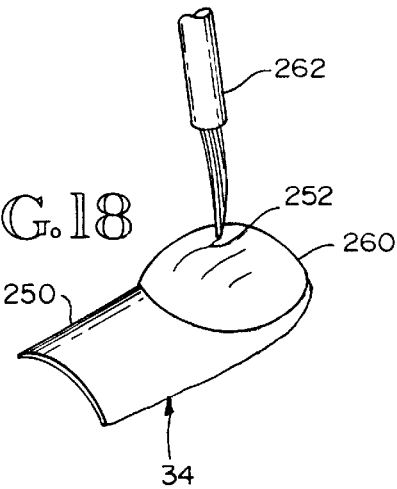
Figure 19:
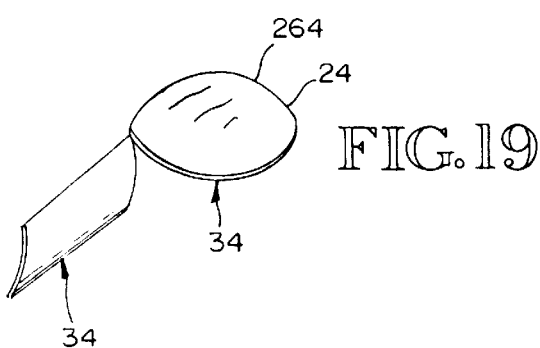
Figure 20:
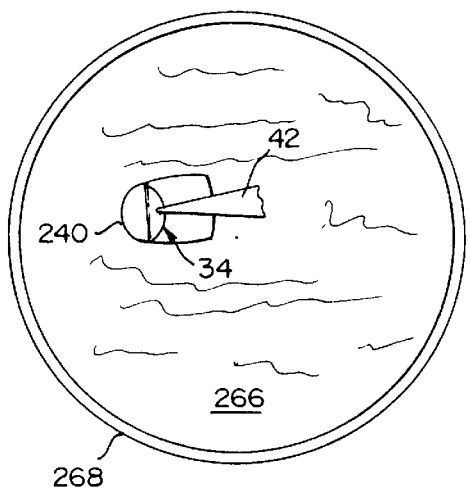
Figure 21:
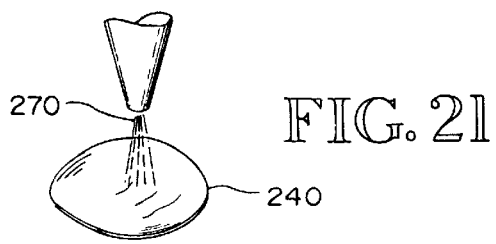

FIG. 15 is a perspective view of the noble metal foil on the front tooth die, partially covered by a then fired porcelain, and the second time of applying a porcelain slurry using a porcelain sable brush to cover over the bald area and further contour the porcelain and porcelain slurry before the second firing;

FIG. 16 is a perspective view of the noble metal foil on the front tooth die when covered by a porcelain slurry, and when being vibrated by using a riffler dental instrument to increase the uniformity of the respective depth portions of the porcelain slurry by eliminating air pockets, etc., and this riffler may also be used at the time of the first application of the porcelain slurry;

FIG. 17 illustrates the removal, from the front tooth die, of the platinum foil matrix and the baked porcelain enamel veneer or laminate, which are still adhered to one another;

FIG. 18 illustrates how characterization is done using a finer pointed brush to apply different shades of porcelain and to create comparable surface textures, with respect to the patient's other teeth not needing restoration, and then another firing of the porcelain is undertaken;

FIG. 19 illustrates how additional shaping of the fired porcelain is undertaken, and also excess metal foil is removed, so a preliminary fitting in a patient's mouth may be undertaken;

FIG. 20 shows how the metal foil matrix and the fired porcelain, after the placement in water, are thereafter separated; and FIG. 21 illustrates how the interior surface of the porcelain veneer or laminate is roughened before the subsequent cementing step is undertaken by sandblasting, in lieu of etching, which also could be undertaken.

DESCRIPTION OF PREFERRED METHOD AND APPARATUS

Selection by the Dentist and Patient's Election to Have a Porcelain Veneer Laminated to the Front Face of One or More of the Front Teeth of the Patient to Aesthetically-Improve the Appearance Thereof.

To avoid the grinding down of a front tooth and the fitting of a crown thereon, the selection of having a porcelain veneer laminated on a front face of a front tooth of a patient has been undertaken for quite some time. One method is called the investment casting method. It is followed to create a cast tooth die upon which a porcelain slurry is distributed and then fired. To obtain the porcelain veneer, the cast tooth die is broken away. On occasions when the porcelain veneer does not fit satisfactory, the investment casting procedure must be undertaken once again. This investment casting method, even when successful the first time, requires considerable skill and a substantial length of time to accomplish. For example of the time involved in using the investment casting method, after the mixture calcium silicate and gypsum bonding materials or phosphate bonding materials has been poured in the impression of a patient's teeth and thereafter has bonded together sufficiently to be handled, this start of an investment die must be placed in a furnace for not less than six hours at 1600° F. before it can be used. Moreover the resulting investment die is very fragile, requiring extreme care when it is being handled as the porcelain slurry is distributed on this investment die and also when this die with the porcelain slurry is being placed into a furnace for the firing of the porcelain.

Also following another method, a porcelain veneer has been created by using a noble metal foil which is burnished over the front face of a front tooth die. The front tooth die is cut away from a die made by pouring die materials in an impression of a patient's teeth. The burnishing has been and is accomplished by using hand held dental tools. The time needed for the burnishing to get the accuracy needed is substantial. The skill level of personnel is very high so they can effectively conform the noble metal foil to the patient's tooth die. After the accurate conforming is completed the noble metal foil matrix is conveniently handled when receiving the porcelain slurry and later when so covered, the noble metal matrix is conveniently entered into a furnace for the firing of the porcelain.

To provide a dentist and his or her patient with yet another method to obtain a porcelain veneer on the front surface of a patient's front tooth and perhaps porcelain veneers on several front teeth, the burnished noble metal foil method has been improved to substantially reduce the overall time, labor, and skill required. The major reduction in time centers on the elimination or substantial elimination of the dental hand tool burnishing efforts undertaken by those persons trying to conform the noble metal foil to the top surface of the patient's front tooth die.

Figure 1:
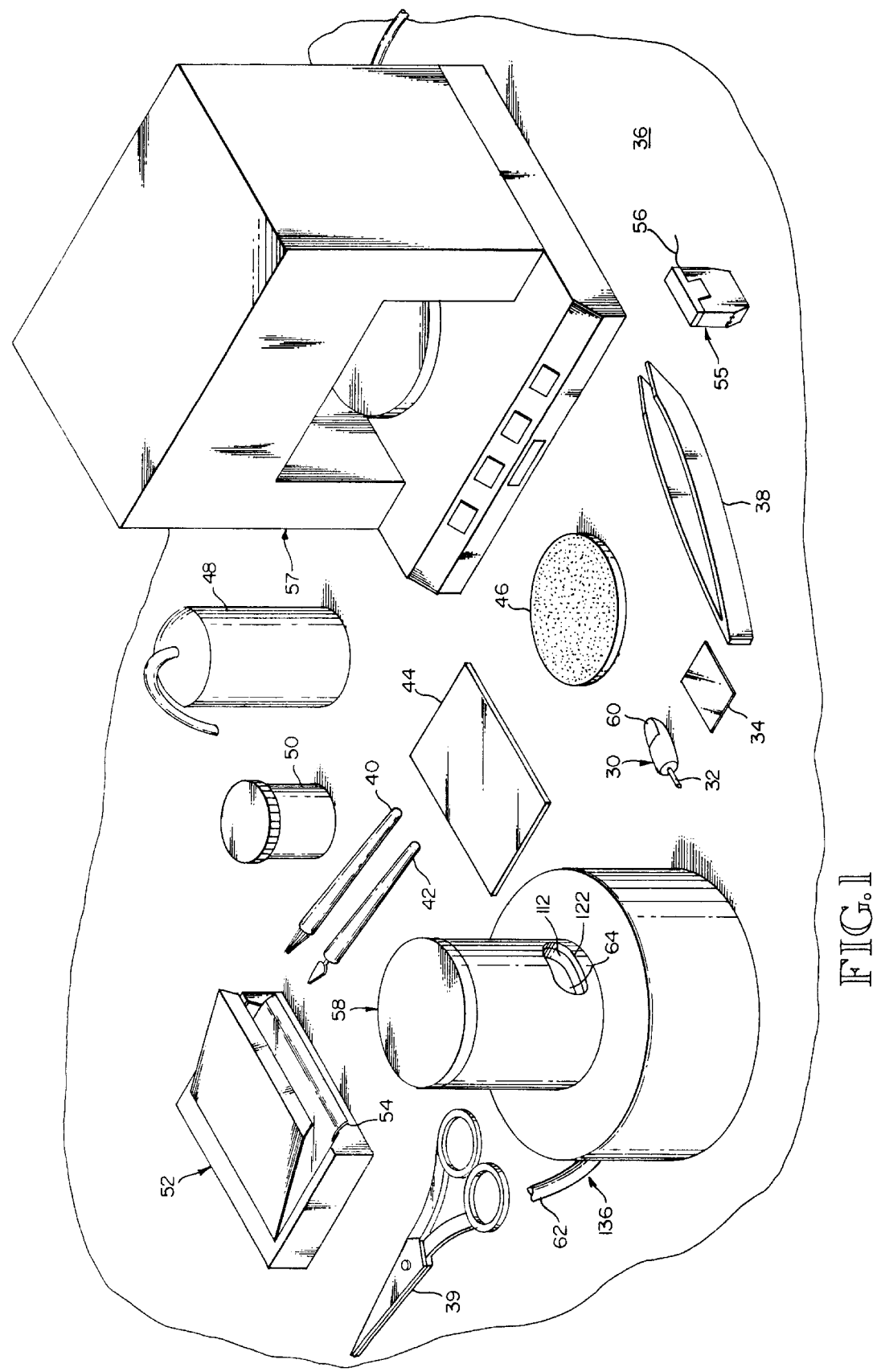
Figure 2:
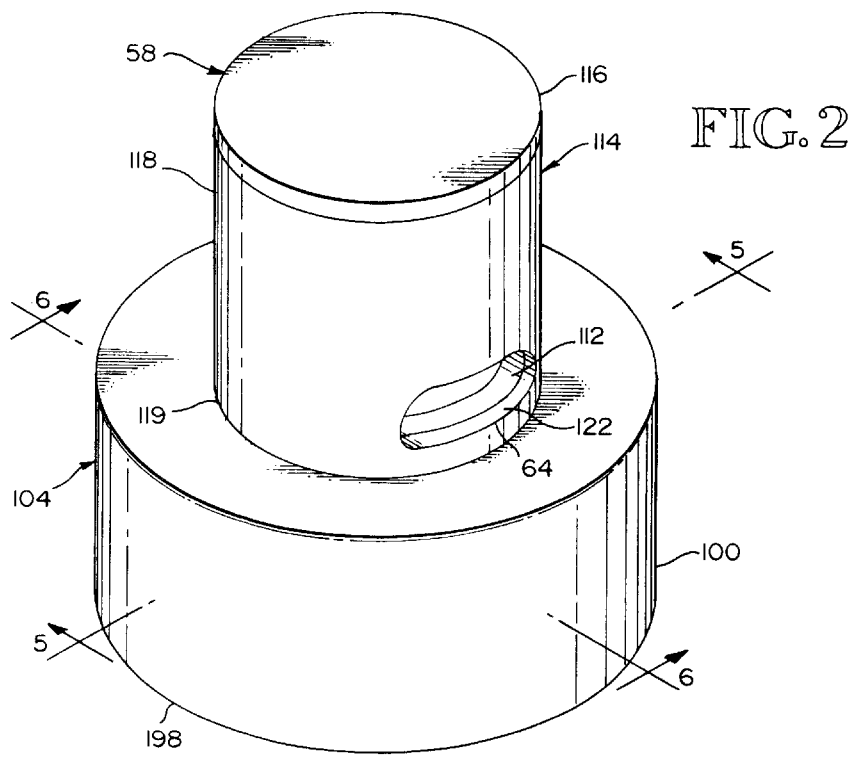

Improved Method of Creating a Porcelain Veneer by Using a Noble Metal Foil Which is Conformed to the Front Surface of a Front Tooth of a Patient by Using Rubber or Rubber-Like Die Inserts Moved Together by an Orbital and Isostatic Force Developed by Utilizing Compressed Air in an Apparatus Having a Piston, Cylinder, and Dies The improved method, also referred to as an improved porcelain laminate system, is described in reference to the drawings, showing first the arrangement in FIG. 1 of some of the apparatuses, hand tools, the supplies, and the patient's front tooth die made available to a person who will be following this improved method and using new apparatus to create a porcelain veneer. The new apparatus is illustrated in FIGS. 2 through 9. Then FIGS. 9 through 21 show how additional steps of the improved method are undertaken.

Apparatuses, Hand Tools, Supplies and Patient's Front Tooth Die

In FIG. 1, a patient's tooth die 30, fitted with a pin 32 is waiting to be fitted with a noble metal foil 34, such as a platinum or palladium foil, on a table top 36. Some of the other items arranged on the table top 36 are: the hand dental tools of tweezers 38, scissors 39, a sable brush 40 for brushing a porcelain slurry, a porcelain knife 42 for cutting porcelain; a glass plate 44 on which a porcelain slurry is formed; a ceramic disc or tray 46 on which items are placed for their heating; a container 48 of distilled water; a container 50 of powdered glass for the porcelain; a box 52 of thin plastic sheets 54; a dispenser 55 of dental floss 56; a dental vacuum fired porcelain furnace 56; and a forming machine 58 operated to conform the noble metal foil 34 to the front surface 60 of the patient's tooth die 30, when an orbital and isostatic force is created using compressed air being supplied through the compressed air line 62. The entry or access 64 of the machine 58 into the interior thereof is only opened when the compressed air supply is turned off, thereby avoiding any injury to the fingers of personnel and/or to their dental tools.

Figure 3:
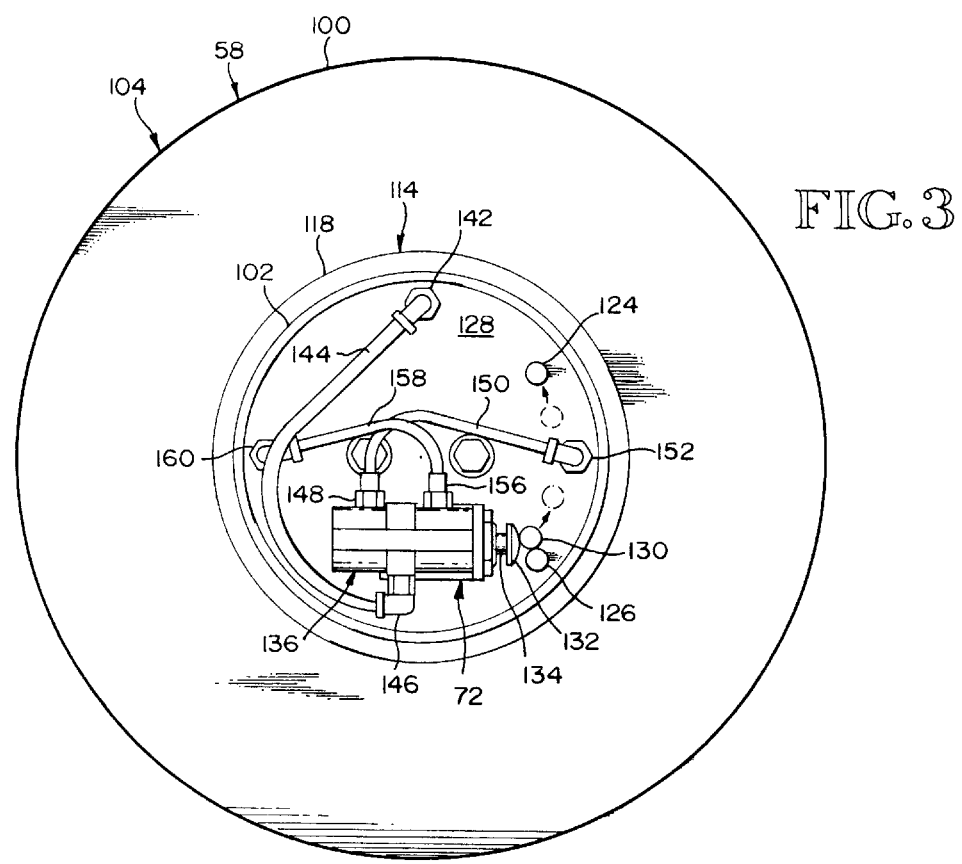
FIG. 3 is an enlarged top view of the forming machine shown in FIGS. 1 and 2, with portions removed, to indicate how the air pressure source line is shut off, via the operation of a valve, which in turn is manipulated as a switching pin is moved along an arc, when carried by one rotatable top portion, of two overlapping hollow cylindrical top portions of this forming machine.

The Preferred Embodiment of the Forming Machine Used in Conforming a Noble Metal Foil, Such as a Platinum or Palladium Foil, to the Front Surface of the Tooth Die of the Patient's Front Tooth The forming machine 58 shown in FIG. 1 positioned on the table top 36, is illustrated further throughout FIGS. 2 through FIG. 8. As shown in FIGS. 1, 2, 4, and 6, there is a through overall access 64 to an open space 66 between die assemblies, i.e. the top die assembly 68, and the bottom die assembly 70, when the compressed air supply, available at a selected constant pressure, from a dental laboratory compressed air system, not shown, via a compressed air line 62 is turned off upon the operation of a compressed air valve 72, as shown in FIG. 3.

The open space 66 is made available to receive a patient's tooth die 30, covered with a cut to size noble metal foil 34, and they in turn, in a shrink like wrapping, are covered with a thin plastic sheet material 54, to keep the patient's tooth die 30 and the noble metal foil 34 clean and accurately positioned together. The thin plastic sheet material 54 itself is kept in position, as portions thereof, extending about the pin 32, are well wrapped using dental floss 56, as shown in FIG. 12, creating the wrapped assembly 74 of the patient's tooth die 30 and the noble metal foil 34. The dental floss 56, in addition to being used to hold the thin plastic material in place, is preferably wound around several times to form a tapered transition filler body 75, commencing at the circumference of the pin 32 and ending at the circumference of the patient's front tooth die 30. This is done to prevent breakage at this location of the patient's front tooth die 30, when later the noble metal foil 34 is being conformed to the front surface 60 of the patient's front tooth die 30.

After this wrapped assembly 74 is entered into the open space 66, using tweezers 38, it is lowered into a receiving space 76 of a rubber or rubber-like silicone material insert 78 of a lower or bottom female die 80 of the bottom die assembly 70. The rubber insert 78 has a surrounding flange 82 to resiliently snap into place in a receiving groove 84 formed in bottom die 80, which is preferably made of aluminum. In direct alignment above is a receiving space 86 of a rubber insert 88 of a higher or top male die 90, of the top die assembly 68. This rubber insert 88 also has a surrounding flange 92 to resiliently snap into place in a receiving groove 94 formed in the top die 90, which is preferably made of aluminum. The rubber insert 78 of the bottom die assembly 70, and the rubber insert 88 of the top die assembly 68, are illustrated separately in FIG. 7 in their spaced apart positions.

When the wrapped assembly 74 of the patient's tooth die 30 and the noble metal foil 34 is well positioned in the elongated receiving space 76 of the bottom die assembly 70, then this bottom die assembly 70 is moved into contact with the top die assembly 68, as shown in FIG. 8. During this movement and while these die assemblies 68, 70 are held together for ten seconds, the created orbital and isostatic force results in accurately conforming the noble metal foil 34 to the front surface 60 of the patient's front tooth die 30.

The preferable way to move bottom die assembly 70 into contact with the top die assembly 68 is by securing the bottom die assembly 70 to a piston assembly 98, movable in turn within a cylinder assembly 100, and utilizing compressed air derived from a compressed air supply, preferably kept at 100 p.s.i., or within a range of 85 to 110 p.s.i., but not greater than 110 p.s.i.

To fulfill the very important safety feature of having the compressed air supply turned off, when the wrapped assembly 74 of the patient's tooth die 30 and the noble metal foil 34 is being positioned through the overall access or entry 64, to eventually be placed in the receiving space 76 of the rubber insert 78 of the female bottom die 80, other portions of the forming machine 58 are arranged for relative rotation. Each of the portions has a respective alike recess or entry which are only aligned for through access through the overall access or entry 64, when the compressed air supply is turned off.

To provide one of these portions, a hollow guiding cylindrical portion or housing 102 is made integrally with the cylinder assembly 100, and located above it, and together they comprise the hollow base member 104. The outside diameter 106 of the cylinder assembly 100 is greater than the outside diameter 108 of the hollow guiding cylindrical housing 102, creating a circular horizontal surface 110 of the hollow base member 104. One of the respective alike recess or entry is the inner entry 112 of this hollow guiding cylindrical housing 102, or of the base member 104.

To limit the arc of the relative circular movement between the covering cap member 114 and hollow guiding cylindrical housing 102, a pair of spaced upstanding stop abutments or pins 124, 126 are positioned on the integral top portion 128 of the hollow guiding cylindrical housing 102. The covering cap member 114, or covering cap assembly 114, has the top 116 thereof equipped with a depending positioning pin 130, which is always, when moved, moving along an arc of travel, which includes the positions of the upstanding stop pins 124, 126.

This arcuate positioning of these upstanding space pins 124, 126, and the depending positioning pin 130, in addition to controlling the extent of the relative rotation between the covering cap member 114 and the hollow guiding cylindrical housing 102, serves in keeping the depending positioning pin 130 in its operating range. Within this range, this pin 130 will only be contacting the extending cammed top portion 132 of the sliding valve stem 134 of the compressed air valve 72 to open this valve 72, when the through overall access 64 is closed, as shown in FIGS. 3 and 8.

As viewed in FIGS. 1, 3, and 5, the overall compressed air system 136, has an incoming compressed air line 62, directing compressed air from a constant pressure source, not shown, of a compressed air system, available in a dental laboratory, to the hollow base member 104. This incoming air line 62 is securely secured to the compressed air intake valve 138, which in turn is securely installed in the hollow base member 104. The incoming compressed air is directed up through an integrally formed compressed air passageway 140, and then through a connecting air fitting 142, and then through a flexible incoming compressed air line 144 to an air intake fitting 146 on the two way compressed air valve 72. Compressed air, upon operation of the air valve 72, is delivered through the air fitting 148, then through the flexible air line 150 to the air fitting 152 and beyond down through an integrally formed compressed air passageway 154 to the cylinder assembly 100 to move the piston assembly 98, to in turn move the bottom die assembly 70, in accomplishing the accurate and quick conforming of the noble metal foil 34 to the front surface 60 of the patient's tooth die 30, as the orbital and isostatic force is created. When the depending positioning pin 130 is moved clear of the extending cammed top portion 132 of the sliding valve stem 134 of the compressed air valve 72, then compressed air is directed through air fitting 156, through flexible air line 158, through air fitting 160 and beyond down through an integrally formed compressed air passageway 162 to the cylinder assembly 100 to move the piston assembly 98 back to the starting position. The interior compressed air passageway ways 140, 162, respectively also serve as air venting passageways depending on the operation of the compressed air valve 72 and the resulting direction of motion of the piston assembly 98.

The several other parts which also comprise the forming machine 58 are observed when viewing FIG. 4 where most of them are illustrated before their assembly. Their assembled positions and locations are particularly shown in FIGS. 5 and 6. On the left side of FIG. 4, from top to bottom, the following parts are illustrated:

The large diameter O-ring 166, and the small diameter O-ring 168 which are both installed in the threaded removable top central ring portion 170 of the top 172 of the cylinder assembly 100;

The hollow piston connecting shaft 174 which slidably passes through the hole 176 in the central ring portion 170 of the top 172;

The compressed air receiving piston 178 having a groove 179 to receive its O-ring 180, a centering recess 182 to position the hollow piston connecting shaft 174, and a center hole 184 to receive a threaded bolt 186. This bolt 186 secures together the piston 178, the shaft 174 and the bottom die 80 of the bottom die assembly 70;

The threaded removable circular bottom 190 of the cylinder assembly 100 having a groove 192 to receive an O-ring 194, which is shown in FIGS. 4, 5 and 6; and The rubber base member 196 which is adhered to the overall base 198 of this forming machine 58 to keep it well positioned on the table top 36.

Then on the right side of FIG. 4, from top to bottom the following parts are illustrated:

The top 116 of the covering cap member 114 or covering cap assembly 114 having a top cap alignment hole 200, which receives a locating alignment pin 204, shown in dotted lines, and having the depending positioning pin 130, also shown in dotted lines. The alignment hole 200, which receives a locating alignment pin 204, is used to make sure the pin 130 is in the correct position upon assembly of the forming machine 58;

The depending cylindrical portion 118 of the covering cap assembly 114 has the lower cap alignment notch 202, which is kept in alignment with the top cap alignment hole 200, and its locating pin 204. Also the outer entry 122 is formed in this depending cylindrical portion 118. The bottom surface 119 of this cylindrical portion 118 and also the covering cap assembly 114 is smooth for movement on the inner portion 111 of the smooth circular horizontal surface 110 of the hollow base member 104;

The hollow base member 104 integrally comprises the cylinder assembly 100 and the hollow guiding cylindrical portion 102 or housing 102. The inner entry 112 is formed in this housing 102 of the hollow base member 104;

On the integral top portion 128 of the hollow guiding cylindrical portion 112 or housing 112, a support bracket 210 is secured in place by fasteners 212 and an upstanding portion 214 thereof has a receiving hole 216 to receive a threaded portion 218 of the two way compressed air valve 72. Upon tightening nut 220, the valve 72 installation is completed;

The respective ports of the respective integrally formed inside compressed air passageways 140, 154, and 162 are shown as they appear on the integral top portion 128;

Also shown in this FIG. 4, are the upstanding spaced stop pins 124, 126, which are secured to the integral top 128 in their definite locations between which the depending positioning pin 130 is confined in its movement;

Extending through the integral top portion 128, are two alike recessed headed holes 222 which receive respective alike threaded fasteners 224, shown in FIG. 5. These fasteners 224 are turned into two alike threaded holes 226 which are formed in the top die 90, to secure the top die assembly 68 in its stationary position illustrated in FIGS. 5, 6, and 8, in the hollow base member 104;

As also viewed in FIG. 4, are the top die assembly 68 and the bottom die assembly 70, each having their respective rubber inserts 88 and 78. The two alike threaded holes 226 are formed in the top die 90 to receive the two alike threaded fasteners 224; and Also a die assemblies alignment pin 228 is tightly fitted in a receiving hole 230 in the top die assembly 68, and slidably guided in a receiving passageway 232, or hole 232, in the bottom die assembly 70, as shown in FIGS. 4 and 5. This alignment pin 228 insures the correct alignment of the respective receiving space 76 of the rubber insert 78 of the lower die 80, and the receiving space 86 of the rubber insert 88 of the top die 90. These rubber inserts 78 and 88 are also shown in FIG. 7 by themselves.

During the assembly of all of these various parts of this forming machine 58, the covering cap member or assembly 114, while still being free to rotate through the short arcuate distance determined by the spaced positioning of the upstanding spaced stop pins 124, 126, is kept from being lifted up and clear of the hollow guiding cylindrical portion or housing 102. This limited motion results when a top capped retaining screw 234 is threaded into and through a threaded hole 236 in the hollow guiding cylindrical portion or housing 102 to extend a short distance beyond into a circumferential internal captive recess 238 of the covering cap member or assembly 114 as shown in FIG. 6.

How the Improved Method is Undertaken of Creating the Porcelain Veneer Using a Noble Metal Foil Which is Accurately and Quickly Conformed to the Front Face of the Patient's Front Tooth Die by Using This Forming Machine This improved method, referred to as an improved porcelain laminate system, for laminating an aesthetically appearing porcelain veneer to the exterior front surface of a person's, i.e. patient's, front tooth, centers on the time and labor saving utilization of this forming machine 58.

When the decision has been made by a person, after first being fully informed by a dentist about having one or more of his or her front teeth improved by the bonding thereon of a porcelain veneer 240 to become a porcelain laminate 240 on a respective person's front tooth, then the person, now a patient, has his or her teeth and jaw impression or impressions made. The impression starting material may be made of polyvinyl silloxane.

Thereafter, preferably two models are made by pouring gypsum powder slurry into the patient's impression at respective times. One of the models may remain as an unaltered reference and backup model. The other model 242, at least may be trimmed and fitted to a base 244 also made of gypsum of a lesser quality then the gypsum used in the models. The fully completed mounted model 246, referred to as the working master model 246, is shown in FIG. 9.

Then one or more of the patient's front teeth dies is cut free from the working master model 246, such as the patient's front tooth die 30, illustrated in FIG. 9, to which a mounting and handling pin 32 has been secured. A hole 248 is made in working master model 246 to receive the mounting and handling pin 32, when a patient's front tooth die 30 is returned to the working master model 246.

Preferably, a special ceramic pencil, not shown, is used to outline on the front surface 60 of the patient's tooth die 30, the front area and shape that is similar to the front area and shape of the patient's front tooth, as shown in FIG. 10.

A noble metal foil 34, such as a platinum foil or a palladium foil, 0.001 inches thick, is selected for placement over and slightly beyond the front surface 60 of the patient's front tooth die 30. Thereafter, the noble metal foil 34 is trimmed, using scissors 39 and/or other cutting tools, to the size, as indicated in FIGS. 10 and 11. The noble metal foil 34 must extend, at least, to the height of the contour or equator of the patient's front tooth die 30. Or stated differently, the noble metal foil 34 must extend, at least, to the boundaries of the front surface 60 of die 30, also referred to as the labial boundaries of the front surface 60 of the die 30.

Preferably, the noble metal foil 34 also extends beyond the top of the front surface 60 of the die 30. This extension is five to six millimeters beyond the gingival location on this die 30, i.e. beyond the top of the front surface 60 of the patient's front tooth die 30. This extended portion 250 of the noble metal foil material 34, is used as a gripping portion to be held by using tweezers 38, when handling this noble metal foil material 34: as a porcelain slurry 252 is brushed on using a sable brush 40; when a drying porcelain slurry 252 is cut by using a porcelain knife; when a fired porcelain portion 256 is being trimmed or shaped by using other dental tools; when the noble metal foil material 34 is to be annealed; when the noble metal foil material 34 and a porcelain slurry 252 are to be placed in a dental vacuum fired porcelain furnace 57; when the noble metal foil 34 and porcelain portion 252, after characterization, are to be fired to obtain the glazing wanted on the final porcelain veneer 240, i.e. the final porcelain laminate 240.

When the noble metal foil 34 has been completely cut, shaped, and sized, it is placed over the front surface 60 of the patient's front tooth die 30. To keep this proper sized noble metal foil 34 in this position, both it and the tooth die 30 are covered with a thin plastic sheet 54 taken from the box 52, as shown in FIG. 1. This thin plastic sheet 54 is drawn tightly about both the noble metal foil 34 and the tooth die 30, in a way to resemble a shrink wrapping. The plastic sheet 54 drawn about the handling and mounting pin 32 is so held in position by wrapping around the pin 32 and the plastic sheet material 54 several turns of dental floss 56 taken from the dispenser 55, shown in FIG. 1.

Preferably more turns of dental floss 56 are wound to create a tapered transition filler body 75, a shown in FIG. 12, commencing at the circumference of the pin 32 and ending at the circumference of the patient's front tooth die 30. This is undertaken, as a precaution, to prevent any possible breakage at this location of the patient's front tooth die 30, when later the noble metal foil 34 is being conformed to the front surface 60 of the patient's front tooth die. Preferably any extra plastic sheet material 54 extending beyond the end of the pin 32 is cut away. This shrink like wrapping of the noble metal foil 34 and the patient's front tooth die 30, also insures that no contaminating unwanted dust or debris will gain access to the noble metal foil 34 or to the patient's front tooth die 30 during the handling operations to follow.

Now the operation of the forming machine 58 is utilized to accurately and quickly conform the noble metal foil 34 to the front surface 60 of the patient's front tooth die 30, saving substantial time and labor. Preferably by using tweezers 38, the wrapped assembly 74 of the noble metal foil 34 and the patient's front tooth die 30, is placed through and beyond the through overall access or entry 64 of the forming machine 58 and down into the receiving space 76 of the rubber insert 78 of the bottom die 80. In reference to a specific embodiment of a forming machine 58, the length of the receiving spaces 76 and 86 is thirty six millimeters and the width is twelve millimeters. The wrapped assembly 74 therefore should not exceed thirty five millimeters in length nor eleven millimeters in width, leaving the one millimeter clearance.

Thereafter, when the tweezers 38 are withdrawn, the person using this forming machine 58 rotates the covering cap member or assembly 114 relative to the hollow guiding cylindrical portion or housing 102, i.e. to the hollow base member 104. At this rotating time the outside entry 122 is moved so it no longer is aligned with the inner entry 112, thereby blocking or eliminating access to the through overall access or entry 64. After this blocking, then the continued relative rotation causes the depending positioning pin 130 to contact the extending cammed top portion 132 of the sliding valve stem 134 of the two way compressed air valve 72. When the depending positioning pin 130 remains in contact with the extending cammed top portion 132 moving it and consequently the sliding valve stem 134, then compressed air from a preferably constant pressure compressed air source, maintained at the preferable pressure of 100 p.s.i., is directed into the forming machine 58. Generally, such a compressed air source is available in dental laboratories. If not, equipment for this purpose will be furnished.

The compressed air flow within the forming machine 58, at the outset is directed to the cylinder assembly 100 to cause the movement of the piston assembly 98, to in turn move the bottom die assembly 70 into contact with the top die assembly 68. The respective bottom die 80 with its rubber insert 78 having its receiving space 76, in which the wrapped assembly 74 of the noble metal foil 34 and the patient's front tooth die 30 has previously been placed, interfits with the respective top die 90 with its rubber insert 88 having the receiving space 86, with these dies serving respectively as female and male die, whereby the overall rubber material of these rubber inserts 78, 88 completely surrounds the wrapped assembly 74 under what is termed an orbital and/or isostatic force.

This conforming of the noble metal foil 34 over and on the front surface 60 of the patient's front tooth die 30 insures, during a ten second holding period, that the noble metal foil 34 is accurately and quickly conformed.

Subsequently the person using this forming machine 58 rotates, in the opposite direction, the covering cap member or assembly 114 relative to the hollow base member 104. At the initial time of this counter rotation, the sliding valve stem 134 moves and the compressed air supply is no longer able to move the bottom die assembly 70 upwardly, and it is retracted to again provide the open space 66. When the counter rotation is completed, the outer entry 122 is aligned with the inner entry 112, and the wrapped assembly 74 of the conformed metal foil 34 and the patient's front tooth die 30 is withdrawn, preferably using tweezers 38, through the now available through overall access or entry 64.

There may be times, when the dental floss is unwound and the plastic sheet material 54 is removed, that the inspection of the noble metal foil 34 will indicate its complete correct conforming. Generally, however, there will be slight folds located near the edges thereof, and these are flattened out preferably using a clean number seven wax spatula. At this time or earlier, the noble metal foil 54 may be entered into a dental vacuum fired porcelain furnace to anneal it.

Following any such hand tool forming, also referred to as burnishing, the noble metal foil 34 and the patient's tooth die 30 are carefully covered and wrapped into another wrapped assembly 74 and conformed again in the forming machine 58 in the same way as previously undertaken. Generally only two such conforming operations are undertaken. If another conforming operation is needed it will be done.

When the conforming passes inspection, then using supplies and equipment shown in FIG. 1, a person selects the color of powdered glass for the porcelain to meet the patient's specifications, from a container 50, and pours it on a glass plate to receive distilled water from a container 48, and then he or she creates a porcelain slurry 252, generally using a porcelain knife during the mixing of the powder and water. When the right color and consistency are reached, then as the conformed noble metal foil 34 is held, preferably by using tweezers 28, a sable brush 40 is used to distribute the porcelain slurry 252 on the top surface of the conformed noble metal foil 34, as shown in FIG. 13. A central area 254 is left clear and called a bald area 254. This procedure is helpful in later compensating for the shrinkage of the porcelain when it is fired. In addition to leaving the bald area 254, the porcelain slurry 252, is partially dried by using tissue to absorb excess water from the porcelain slurry 252, and then as shown in FIG. 14, cuts are made at spaced locations by using a porcelain knife 42. This procedure is also helpful in later compensating for the shrinkage of the porcelain when it is fired.

The firing is undertaken preferably in a dental vacuum fired porcelain furnace 57, which is shown in FIG. 1. Preferably, the temperature is held constant at 1800° F., although a temperature at 1750° F. is considered high enough.

Then the porcelain slurry 252 is applied for a second time using the sable brush 40, as shown in FIG. 15, and the bald area 254 is filled in, and also cuts, cracks, are filled in, and another layer, via the porcelain slurry, is commenced over the first fired porcelain portion, as necessary to increase the eventual depth where selected, of the porcelain.

At any time when porcelain slurry 252 is brushed on, and preferably at this time, the noble metal foil 34, the porcelain slurry 252 and the supporting patient's front tooth die 30, are vibrated, as shown in FIG. 16, by using a riffler dental instrument 258 to increase the uniformity of the respective depth portions of the porcelain slurry 252, by eliminating air pockets, and other irregular distributions of the porcelain slurry 252.

Then the noble metal foil 34, and the porcelain slurry, when separated from the patient's front tooth die, as shown in figure 17, are placed on the ceramic disc 46 or ceramic tray 46 by using tweezers 38, and thereafter the ceramic tray 46, so loaded, is placed in the dental vacuum fired porcelain furnace 57 for a second firing of the porcelain slurry 252. When the firing is completed and the noble metal foil 34 having the second fired porcelain 260 is cool, the porcelain veneer 240, or porcelain laminate 240, is inspected.

If the dental laboratory is in a dental office or adjacent thereto, or close nearby, the porcelain veneer 240 and the noble metal foil may be taken to a patient for a preliminary fitting and inspection.

If the porcelain veneer 240 passes inspection it then may be fired again while on the noble metal foil 34 to acquire a glossy glaze.

Often before this firing to acquire the glossy glaze, characterization may be undertaken, which means one or more steps may be undertaken, such as: adding additional porcelain slurry, sometimes of a different color or colors at selected locations, such as at the incisal edge, preferably using a finer pointed sable brush 262, as illustrated in FIG. 18; and/or matching favorable irregularities of the surface of the porcelain veneer 240 may be created. The final firing is undertaken to acquire the glaze of the last fired porcelain 264. When this near final inspection occurs and the porcelain veneer 240, soon to become the porcelain laminate 240, meets the dentist's specifications, tailored to meet his patient's requirements, then as shown in FIG. 19, selected dental instruments may be used to remove the excess noble metal foil 34 that still may be present, and/or also to shape the porcelain veneer 240.

Then at this time the porcelain veneer 240 on the noble metal foil 34 may be fitted to the patient's front tooth to check its prospective fit. Also at this time the thickness of the noble metal foil 34 is comparable to the prospective thickness of the bonding material to be used to bond the porcelain veneer 240 to the front surface of the patient's front tooth, where it will serve as an excellent aesthetically pleasing porcelain laminate 240 for many years, before rebonding might become necessary.

If the fitting, by slight chance needs improvement, the porcelain veneer 240 is still well manipulated, while on the noble metal foil 34. However, generally at this time, the porcelain veneer 240 meets or exceeds expectations and specifications, and it is separated from the noble metal foil 34, often referred to as the noble metal foil matrix 34, as shown in FIG. 20, preferably using a selected instrument 42, and in the presence of water 266 in a dish 268.

The separated porcelain veneer 240 is carefully handled and a sticky wax is applied to the front glazed surface thereto. Thereafter, continuing on the careful handling, the interior of the porcelain veneer 240 is roughened, either by sandblasting using aluminum oxide particles 270, as shown in FIG. 21, or by etching using a forty five percent hydrofluoric acid, subsequently rinsed.

The sticky wax is removed in icy cold water, and the porcelain veneer 240 is well cleaned. It is then ready for bonding to the patient's front tooth.

The bonding is generally undertaken by using an available light curing bonding material, which is clear. At this time, however, sometimes a bonding material of this light curing type is selected which has color to possibly add a last increment of characterization to the resulting bonded porcelain laminate 240, which will be bonded, i.e. well secured, to a patient's front tooth.

Information Regarding a Specific Model of the Forming Machine Referred to as a Dental Forming Machine The forming machine 58, also referred to as the dental forming machine 58, in respect to a preferred specific embodiment or model has a base diameter of eight and three quarters of an inch, and the cylinder-piston portion stands seven inches high. It weighs nineteen pounds.

The dimensions of the space or volume into which the wrapped assembly 74 of the noble metal foil 34 and the patient's front tooth die are placed, before the orbital and isostatic forces become effective in causing the rubber of the rubber inserts of the dies to forcefully surround this wrapped assembly 74, is one half an inch wide, and one and one half an inch long, i.e. twelve millimeters wide and thirty six millimeters long.

The compressed air, at preferably one hundred pounds per square inch, enters the cylinder to move the piston, which has an active piston area of slightly over forty four square inches. Therefore the compressive force created exceeds four thousand four hundred pounds. This sizeable force is concentrated, via the movement of the dies, to be ultimately effective in the limited area, where the wrapped assembly 74 is positioned, whereby the noble metal foil 34 is accurately and quickly conformed to the front surface 60 of the patient's front tooth die 30 in ten seconds. Yet the conforming force remains below the force necessary to crush the patient's tooth die.

With the compressed air supply being well maintained, preferably at one hundred pounds per square inch, the person using this dental forming machine 58, knows he or she will quickly, accurately, and conveniently, acquire the conforming of the noble metal foil 34 to the front surface 60 of the patient's tooth die 30, at all times.

Brief Summary of This Porcelain Laminate Method or System and the Apparatus Used Which Centers on the Forming Machine 58

When this forming machine 58 is available in a dental laboratory, wherever it may be located, and preferably nearby a dentist's office, it is readily and safely used to very accurately and quickly conform a noble metal foil 34, into a handily used noble metal foil matrix 34 in at least one ten second time period, and perhaps two, and possibly three respective ten second time periods, to achieve an excellent fitting noble metal foil 34. Then when the porcelain veneer 240 is separated from the noble metal foil matrix 240, and its thickness is substituted by the thickness of the light curing bonding agents, the excellent fitting continues of the then porcelain veneer 240, which upon light bonding remains for a long time as an excellent aesthetically appearing porcelain laminate 240 on a person's front tooth. Moreover, as necessary, other front teeth are so fitted with respective aesthetically appearing porcelain laminates 240.

All of the many dental instruments and apparatuses already in use are still used, and all the dental materials are still used. However, the distribution of the porcelain slurry, in reference to leaving the bald area 254 is different. Also the earlier checking of the correct fitting is possible. Also additional characterizations are possible.

Yet in reference to the quick, constant and accurate conformation steps undertaken when using the forming machine 58, there is a substantial reduction of the overall time and the skilled labor required in making excellent porcelain veneers 240 to meet exacting specifications in reaching an aesthetially appearing porcelain laminate 240 on a person's front tooth.

By the substantial elimination of the time consuming hand instrument burnishing procedures, the utilization of noble metal foil conforming procedures, using this forming machine, will be used more often. These noble metal foil procedures, or steps, should be selected and followed, rather than following the investment casting procedures, or steps, which require more time to perform. Moreover, the investment castings are broken away to acquire the porcelain veneer. Therefore if the fitting of the porcelain veneer is not satisfactory, a new patient's tooth die must be made, again, following essentially the entire investment casting procedures, steps, or method.

I claim:

1. A forming machine used in quickly and accurately conforming a noble metal foil to a front surface of a dental patient's front tooth die, comprising:
   a. a hollow housing;
   b. a combined assembly of a cylinder assembly and a piston assembly arranged and secured in part within the hollow housing;
   c. a combined assembly of a top die assembly and a bottom die assembly arranged within the hollow housing and secured in part to the combined assembly of a cylinder assembly and the piston assembly;
   d. two rubber or rubber-like material inserts, one for each respective top die assembly and each respective bottom die assembly, which are formed to transit an orbital and an isostatic force to and about a noble metal foil and a dental patient's front tooth die, to accurately and quickly conform a noble metal foil to a front surface of a dental patient's front tooth die; and
   e. compressed air handling components to utilize compressed air to operate the piston assembly within the cylinder assembly, and thereby to move the two rubber inserts into full contact with a noble metal foil and the patient's front tooth die, creating an orbital and isostatic force, which accurately and quickly conforms a noble metal foil to a front surface of a patient's front tooth die.

2. A forming machine, as claimed in claim 1, wherein the respective rubber inserts are formed with like receiving spaces to receive and to position a noble metal foil and a dental patient's front tooth die to receive an orbital and an isostatic force.

3. A forming machine, as claimed in claim 2, wherein the respective rubber inserts are fitted into a respective top metal die and a bottom metal die, of the respective top die assembly and bottom die assembly.

4. A forming machine, as claimed in claim 3, wherein the respective rubber inserts each has a surrounding flange, and each metal die has a receiving groove to receive a respective surrounding flange of a respective rubber insert.

5. A forming machine, as claimed in claim 1, comprising, in addition, a covering cap assembly for slidably and rotatably fitting over the hollow housing, and both the covering cap assembly and the hollow housing having a respective entry, which are aligned to provide a through overall access to the interior of the hollow housing and to an open space, which is created, when the combined assembly of the top die assembly and bottom die assembly is in an open position to receive a noble metal foil and a dental patient's tooth die for a subsequent conforming of a noble metal foil to a front surface of a dental patient's front tooth die.

6. A forming machine, as claimed in claim 5, wherein the covering cap assembly has a depending pin which will contact a compressed air handling component to obtain compressed air to operate the piston assembly, only after the entry of the covering cap assembly has been moved away from the entry of the hollow housing, thereby closing the previously opened through overall access to the interior of the hollow housing,
   whereby no dental instrument nor fingers of a person will remain in the path of a die being moved by a piston of the piston assembly into contact with another die when compressed air is being utilized.

7. A forming machine, as claimed in claim 6, wherein the hollow housing has upstanding spaced stop pins, which serve to limit the travel of the depending pin of the cap assembly to the distance between the upstanding spaced stop pins.

8. A forming machine, as claimed in claim 7, wherein the upstanding spaced stop pins are positioned on an arcuate travel line along which the depending pin travels.

9. A forming machine, as claimed in claim 6, wherein the compressed air handling component contacted by the depending pin of the covering cap assembly is a two way compressed air valve having an extended slide valve stem which is contacted, by the depending pin to be moved to change the valve setting, thereby opening the valve to pass compressed air to the combined assembly of a cylinder assembly and a piston assembly to cause movement of the combined top die assembly and bottom die assembly, creating the orbital and isostatic force ultimately applied by the two rubber inserts which surround a noble metal foil and a patient's front tooth die, and thereby a noble metal foil is accurately and quickly conformed to a front surface of a patient's front tooth die.

10. A forming machine, as claimed in claim 1, wherein the hollow housing has a large diameter and volume base portion to receive the combined assembly of a cylinder assembly and a piston assembly, and a smaller diameter and volume top portion to receive the combined top die assembly, whereby the piston assembly area which receives the compressed air at a high pressure serves in creating a resulting large force which moves the piston assembly to in turn move the respective die assemblies together, to effectively conform a noble metal foil to a front surface of a patient's front tooth die.

11. A forming machine used in quickly and accurately conforming a noble metal foil to a front surface of a dental patient's front tooth die, comprising:
   a. a hollow housing having a larger diameter cylindrical portion below and a smaller diameter cylindrical portion above;
   b. a combined assembly of a cylinder assembly and a piston assembly integral in part, secured in part, and arranged completely within the hollow housing, with the cylinder assembly being within the larger diameter cylindrical portion below, and with the piston assembly being essentially within the larger diameter cylindrical portion and extending partially into the smaller diameter cylindrical portion above;
   c. a combined assembly of a top die assembly and a bottom die assembly arranged within the hollow housing, having the top die assembly secured to the smaller diameter cylindrical portion at the top thereof, and having a bottom die assembly secured to the piston assembly, and
   each die assembly has a metal die portion, and
   each metal portion has a rubber insert portion, and
   each rubber insert portion has a receiving space to receive a dental patient's front tooth die covered on the top thereof with a noble metal foil; and
   d. compressed air components to utilize compressed air to operate the piston assembly within and beyond the cylinder assembly, whereby the bottom die assembly is moved into contact with the top die assembly, thereby moving the rubber insert portions into full contact with both a noble metal foil and the dental patient's front tooth die, creating an orbital and an isostatic force, which accurately and quickly conforms a noble metal foil to a front face of a dental patient's front tooth die.

12. A forming machine, as claimed in claim 11, comprising, in addition, a covering cap assembly for slidably and rotatably fitting down above the smaller diameter cylindrical portion above of the hollow housing, and both the covering cap assembly and the smaller diameter cylindrical portion above of the hollow housing, each having a respective entry, which are aligned to provide a through overall access to the interior of the hollow housing, and to an open space therein, which is created, when the combined assembly of the assembly and bottom die assembly is in an open position to receive a noble metal foil and a dental patient's front tooth die for a subsequent conforming of a noble metal foil to a front surface of a patient's front tooth die.

13. A forming machine, as claimed in claim 12, wherein the covering cap assembly has a depending positioning pin which will contact a compressed air handling component to obtain compressed air to operate the piston assembly, only after the entry of the covering cap assembly has been moved away from the entry of the hollow housing, thereby closing the previously opened through overall access to the interior of the hollow housing, whereby no dental instrument nor fingers of a person will remain in the path of a die being moved by a piston of the piston assembly into contact with another die when compressed air is being utilized.

14. A forming machine, as claimed in claim 13, wherein the smaller diameter cylindrical portion above, on the top thereof, has upstanding spaced stop pins, which serve to limit the travel of the depending positioning pin of the covering cap assembly to the distance between these upstanding spaced stop pins.

15. A forming machine, as claimed in claim 14, wherein the upstanding spaced stop pins are positioned on an arcuate travel line along which the depending positioning pin travels.

16. A forming machine, as claimed in claim 15, wherein the compressed air handling component contacted by the depending positioning pin of the covering cap assembly is a two way compressed air valve, having an extended slide valve stem, which is contacted by the depending positioning pin, to be moved to change the valve setting, thereby opening the valve to pass compressed air to the combined assembly of the cylinder assembly and the piston assembly, to cause movement of the combined assembly of the top die assembly and the bottom die assembly, creating an orbital and isostatic force, ultimately applied by the two rubber inserts, which surround a noble metal foil and a dental patient's front tooth die, and thereby a noble metal foil is accurately and quickly conformed to a front surface of a patient's front tooth die, and this valve opens only when the through overall access has been closed.

17. A forming machine, as claimed in claim 16, wherein the incoming compressed air coming from a constant pressure source of compressed air, is maintained at a pressure which insures that the resulting force applied to the patient's front tooth die remains below the force needed to crush the patient's front tooth die, thereby insuring that the patient's front tooth die remains available throughout the conforming steps undertaken to accurately conform the noble metal foil to the front face of the patient's front tooth die.

* * * * *